(12) United States Patent
Liou et al.

(10) Patent No.: US 8,420,136 B2
(45) Date of Patent: Apr. 16, 2013

(54) HERBAL PREPARATION FOR ANEMIA AND A MANUFACTURE METHOD THEREOF

(75) Inventors: Shorong-Shii Liou, Kaohsiung (TW); I-Min Liu, Kaohsiung (TW); Chia-Ju Chang, Kaohsiung (TW); Wei-Chih Tang, New Taipei (TW)

(73) Assignee: Han Sheng Biotech Co., Ltd., Pingtung County (TW)

( * ) Notice: Subject to any disclaimer, the term of this patent is extended or adjusted under 35 U.S.C. 154(b) by 0 days.

(21) Appl. No.: 13/174,930

(22) Filed: Jul. 1, 2011

(65) Prior Publication Data

US 2013/0004598 A1 Jan. 3, 2013

(51) Int. Cl.
*A61K 36/00* (2006.01)
*A61K 36/254* (2006.01)

(52) U.S. Cl.
USPC .......................................... 424/728; 424/725

(58) Field of Classification Search .................. None
See application file for complete search history.

(56) References Cited

U.S. PATENT DOCUMENTS

| 5,081,129 | A | 1/1992 | Rozencwaig et al. |
| 6,436,378 | B1 | 8/2002 | Mahashabde et al. |
| 7,585,527 | B2 | 9/2009 | Venkataraman et al. |
| 7,709,031 | B2 | 5/2010 | Greenway et al. |
| 2005/0148088 | A1 * | 7/2005 | Ong .............................. 436/96 |

FOREIGN PATENT DOCUMENTS

| CN | 1876147 A | * | 12/2006 |
| CN | 101606703 A | * | 12/2009 |
| KR | 669233 B1 | * | 1/2007 |

* cited by examiner

*Primary Examiner* — Qiuwen Mi
(74) *Attorney, Agent, or Firm* — Alan Kamrath; Kamrath IP Lawfirm, P.A.

(57) ABSTRACT

A herbal extract for anemia is obtained by a process including steps of drying, by providing a herbal material comprising dry mulberry and dry *Acanthopanax senticosus* in a weight ratio of 2:1 to 1:2, with the water content of the herbal material lower than 10%; extracting, by soaking the herbal material into a solvent to obtain a liquid extract, with the weight ratio between the herbal material and the solvent being 1:10 to 1:5; and condensation, by condensing the liquid extract to obtain a herbal extract.

8 Claims, 1 Drawing Sheet

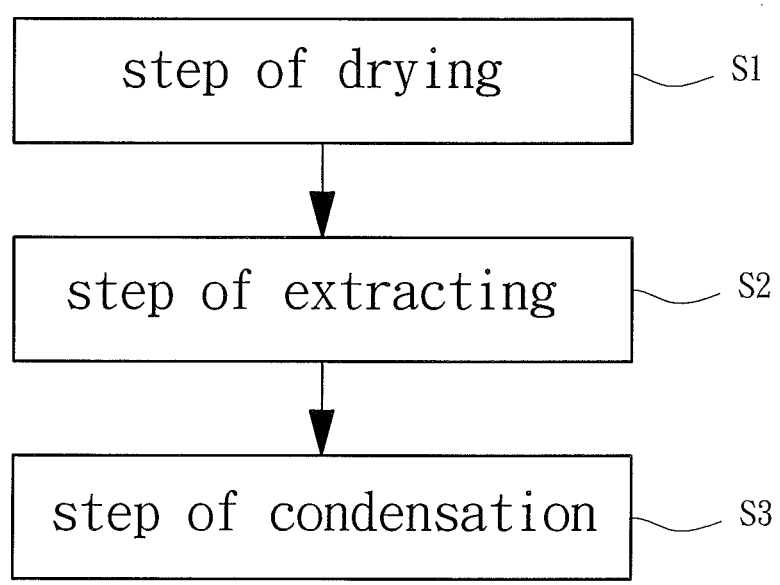

HERBAL PREPARATION FOR ANEMIA AND A MANUFACTURE METHOD THEREOF

BACKGROUND OF THE INVENTION

1. Field of the Invention

The present invention relates to a herbal preparation for anemia and, more particularly, to a herbal extract obtained from mulberry and *Acanthopanax senticosus* and a medication comprising the herbal extract for therapy or prophylaxis of anemia.

2. Description of the Related Art

Anemia, also known as aneamia, refers to a decrease in number of red blood cells (RBCs), hemoglobin in blood, or oxygen-binding ability of each hemoglobin molecule. Anemia may result in hypoxia in organs, poor biochemical response in tissues and finally leading to various disorders, such as head ache, dizziness, palpitation, somnolence, and paralysis in a hand and a foot. According to the definition of the World Health Organization (WHO), a standard quantity of hemoglobin in blood is 13 g/dl in men, and 12 g/dl in women, and therefore, a lower level than the standard quantity of hemoglobin is anemia.

Anemia is a common disorder in blood, and is usually divided into two types, including heritage anemia and non-heritage anemia. Generally, conventional therapy of heritage anemia is mainly based on bone marrow transplant and medicine. Yet, non-heritage anemia is treated by oral supplementation of hemopoietic materials, such as iron, folic acid, vitamin C, vitamin B6, B12 or vitamin E for the sake of maintaining the hemopoiesis in bodies.

In traditional Chinese medicine, the heart, being a center of blood circulation; the liver, being a storage organ of blood; and the spleen, being a key organ in hemopoietic system; all play a significant role in anemia. As a result, Chinese herbal medicine for disorders of the heart, liver and spleen, for example, ginseng, *Codonopsis pilosula* Nannf., Chinese angelica, *Rehmannia glutinase*, longan, red date, wolfberry (*Lycium barbarum*), ejiao and mulberry, are usually used in the treatment of anemia.

In conventional art, herbal preparations of "siwu tang," comprising Chinese angelica, *Ligusticmchuanxiong franch* Hort., Chinese peong (*Paeonia lacciflora*), and *Rehmannia Glutinosa*; "siwutang adduct," comprising chinese angelica, *Ligusticmchuanxiong franch* Hort., Chinese peong, Chinese knotweed (*polygonum multiflorm*), black date, wolfberry,*Rehmannia glutinosa* and *Codonopsis pilosula* Nannf.; "angelica tang," comprising Chinese angelica, *astragalus membranaceus*, or "ren shen yang rong tang," comprising ginseng, atractylodes, *Radix paeoniae* Alba (supefine), *Wolfiporia extense, Astragalus membranaceus*, licorice (*Glycyrrhiza glabra*), cinnamon, Chinese angelica, schisandraceae (*Schisandra chinesis*), *Ziziphus jujube* Mill., and ginger (*Zingiber officinale*), are commonly used in traditional Chinese medicine to treat of anemia. However, the refining and decocting process of those herbal preparations is complicated, time consuming and wasteful in cost. As a result, due to the inconvenience of those herbal preparations, the herbal medicines for anemia are less popularized and unacceptable to the mass of population.

SUMMARY OF THE INVENTION

The primary objective of this invention is to provide a herbal extract for anemia, which is obtained from natural herbal medicine and is capable of improving the symptoms of anemia due to the natural medical properties of those natural herbal medicines.

The secondary objective of this invention is to provide a medication for anemia, which is easy to be taken by patients so that the herbal medicine will be more commonly and easily acceptable by general patients.

Another objective of this invention is to provide a manufacture method of a herbal extract for anemia, in which, the herbal extract can be successfully obtained via an easy, convenient and time-and-cost saving process.

A herbal extract for anemia obtained by a process comprises steps of drying, by providing a herbal material comprising dry mulberry and dry *Acanthopanax senticosus* in a weight ratio of 2:1 to 1:2, with the water content of the herbal material lower than 10%; extracting, by soaking the herbal material into a solvent to obtain a liquid extract, with the weight ratio between the herbal material and the solvent being 1:10 to 1:5; and condensation, by condensing the liquid extract to obtain a herbal extract.

A manufacture method of a herbal extract for anemia comprises steps of drying, by providing a herbal material comprising dry mulberry and dry *Acanthopanax senticosus*, with the water content of the herbal material being lower than 10%; extracting, by soaking the herbal material into a solvent to obtain a liquid extract, with the weight ratio between the herbal material and the solvent being 1:10 to 1:5; and condensation, by condensing the liquid extract to obtain a herbal extract.

A medication for anemia comprises a herbal extract; and a medical acceptable excipient.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The present invention will become more fully understood from the detailed description given herein below and the accompanying drawings which are given by way of illustration only, and thus are not limitative of the present invention, and wherein:

SOLE FIGURE is a diagram illustrating a manufacture method of a herbal extract for anemia in the present invention.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

With reference to the SOLE FIGURE, the present invention provides a manufacture method of a herbal extract for anemia, which comprises a step of "drying S1," a step of "extracting S2," and a step of "condensation S3".

In the step of "drying S1," mulberry and *Acanthopanax senticosus* are prepared and dried individually till the water content of the mulberry and the *Acanthopanax senticosus* decrease lower than 10%, in order to obtain a dry mulberry and a dry *Acanthopanax senticosus*. Then, a herbal material is obtained by combining the dry mulberry with the dry *Acanthopanax senticosus* in a ratio of 2:1 to 1:2.

Mulberry, also known as *Morus alba* L., is generally used as a traditional and folk medicine. Mulberry is believed to have curative effects on liver or kidney diseases, anemia, tinnitus, strain of waist, insomnia, and disorders of digestion. Mulberry, particular to dry mulberry, is rich in iron, with around 42.5 mg of iron per 100 g of dry mulberry, and which is dramatically beneficial to hematopoiesis in organisms.

*Acanthopanax senticosus*, commonly referring to roots, stems or leaves of *Acanthopanax senticosus*, has a variety of medicinal properties especially in disorders of the spleen and kidney, ache in the waist and knee, edema, anorexia, insomnia, and the flu.

More precisely, in the step of "drying S1," the mulberry and *Acanthopanax senticosus* can be dried via a lyophilization, spray drying, evaporation or heating drying. In the present embodiment, *Acanthopanax senticosus* of the present invention is soaked in a kind of ricewine, named "HUANGIU" for 22 to 26 hours, followed by decocting at a circumstance of high pressure and high temperature to obtain a decoction of *Acanthopanax senticosus*. the decoction of *Acanthopanax senticosus* and mulberry are dried separately via a lyophilization to obtain the dry mulberry and the dry *Acanthopanax senticosus*. With such arrangement, the activity of medical properties in mulberry and *Acanthopanax senticosus* can be significantly increased, to be easily extracted in the following step of "extracting S2".

In the step of "extracting S2," the herbal component, comprising the dry mulberry and the dry *Acanthopanax senticosus* in a ratio of 2:1 to 1:2, is soaked in a solvent to obtain a liquid extract, with the weight ratio between the herbal material and the solvent preferably being set at 1:10 to 1:5. In this way, the active medical properties of mulberry and *Acanthopanax senticosus* can be easily obtained from the liquid extract. The solvent of the present invention can be water, methanol ethanol acetone, ethane, propane, butane, hexane, petroleum, or benzene. In the present embodiment, a mix of 50 g dry mulberry and 80 g dry *Acanthopanax senticosus* is extracted by 1 liter of distilled water under a process of sonication for 8 hours, for the sake of removing impurities in mulberry or *Acanthopanax senticosus*, and obtaining the liquid extract of the present invention. With the liquid extract of the present invention, it is sufficient for use in the pharmaceutical industry, by manufacturing the liquid extract into any medicament or health product for anemia.

In the step of "condensation S3," the liquid extract is condensed to obtain a herbal extract for anemia. As an example, the condensation of the liquid extract can be performed by evaporation or heating drying. In the present embodiment, the liquid extract is condensed via a process of evaporation, in order to remove solvent from the liquid extract and to obtain the herbal extract of the present invention. With such condensation, the herbal extract comprising a high concentration of medical properties of mulberry and *Acanthopanax senticosus* is successfully obtained, and which will be more significant in use by pharmaceutical industries.

In the next paragraphs, the benefits of the herbal extract in therapy or prophylaxis of anemia are demonstrated in an animal trial. In the present embodiment, male and 8-week-old Wistar rats purchased from the National Laboratory Animal Center in Taiwan are prepared, housed at a standard laboratory environment, such as keeping 25±1° C. and with a 12 hours light/dark cycle, and injected subcutaneously with phenylhydrazine (PHZ) once a day for four days, with a dosage of injection being set up at 40 mg per kilogram of rat. With such injection, the membrane of erythrocyte (also known as red blood cell; RBC) in rats will be destroyed due to the oxidization of the PHZ, and, accordingly, the number of erythrocyte in rats will decrease till lower than $4 \times 10^7$ μl.

With reference to TABLE 1, untreated rats and PHZ-treated rats are randomly assigned into 7 groups, including A0, being a control and having untreated rats fed with chow diet during the trial; A1, having PHZ-treated rats fed with chow diet during the trial; A2, having PHZ-treated rats fed with mulberry extract only, with a dosage of the mulberry extract being set up at 1.0 g per kilogram of rat per day during the trial; A3, having PHZ-treated rats fed with *Acanthopanax senticosus* extract during the trial, with a dosage of the *Acanthopanax senticosus* being set up at 1.0 g per kilogram of rat per day; A4, having PHZ-treated rats fed with the herbal extract of the present invention during the trial, with a weight ratio between mulberry and *Acanthopanax senticosus* being 1:1 in the herbal extract; AS, having PHZ-treated rats fed with the herbal extract of the present invention during the trial, with a weight ratio between mulberry and *Acanthopanax senticosus* being 1:2 in the herbal extract; and A6, having PHZ-treated rats fed with the herbal extract of the present invention during the trial, with a weight ratio of mulberry and *Acanthopanax senticosus* being 2:1 in the herbal extract of the present invention. In the present embodiment, the herbal extract of the present invention is dissolved in distilled water at first, and then is directly given to rats in groups (A4) to (A6) via gavage feeding. After one weeks week of the animal trial, blood of rats in groups (A0) to (A6) are taken respectively to carry out various examinations of blood, such as RBC count, hemoglobin, and hematocrit, by using a heamatoginal analyzer F-800 (Sysmex, Tokyo, JAPAN).

TABLE 1

Groups Arrangements of (A0) to (A6)

| Groups | Treatment | Ratio of Mulberry and *Acanthopanax senticosus* |
|---|---|---|
| A0 | 1 ml chow diet | — |
| A1 | 1 ml how diet | — |
| A2 | mulberry extract | — |
| A3 | *Acanthopanax senticosus* extract | — |
| A4 | herbal extract | 1 □ 1 |
| A5 | herbal extract | 1 □ 2 |
| A6 | herbal extract | 2 □ 1 |

In TABLEs 2 to 4, the number of RBC, and levels of hemoglobin and hemmatocrit of rats in groups (A0) to (A6) are summarized individually. It is noted that rats with PHZ injection show dramatically low level in their number of RBC, hemoglobin and hemmatocrit. However, with treatment of the herbal extract of the present invention, those pathological symptoms are significantly improved, especially with treatment of the herbal extract comprising mulberry and *Acanthopanax senticosus* in a weight ratio of 2:1 (see data of A6). It is verified that the herbal extract of the present invention has medical properties in anemia. Also, with the treatment of the herbal extract, it is sufficient to promote the levels of RBC, hemoglobin and hemmatocrit in organisms, to improve the symptoms of anemia.

TABLE 2

RBC Counts in groups (A0) to (A1)

| Groups | RBC ($\times 10^6$ cells/μl) | |
|---|---|---|
| | Day 0 | Day 7 |
| A0 | 7.58 ± 0.33$^a$ | 7.70 ± 0.47$^a$ |
| A1 | 3.68 ± 0.17 | 4.67 ± 0.25 |
| A2 | 3.53 ± 0.24 | 5.89 ± 0.44$^a$ |
| A3 | 3.63 ± 0.36 | 5.63 ± 0.47$^a$ |
| A4 | 3.66 ± 0.28 | 6.01 ± 0.27$^a$ |
| A5 | 3.39 ± 0.32 | 7.04 ± 0.46$^a$ |
| A6 | 3.54 ± 0.28 | 7.10 ± 0.35$^a$ |

$^a p < 0.05$

TABLE 3

Levels of Hemoglobin in Groups (A0) to (A6)

| Groups | Hemoglobin (g/dl) | |
|---|---|---|
| | Day 0 | Day 7 |
| A0 | 15.93 ± 0.37$^a$ | 16.17 ± 0.30$^a$ |
| A1 | 11.07 ± 0.46 | 10.50 ± 0.26 |
| A2 | 10.68 ± 0.54 | 12.34 ± 0.29$^a$ |
| A3 | 10.59 ± 0.38 | 11.40 ± 0.32$^a$ |
| A4 | 11.09 ± 0.61 | 12.70 ± 0.16$^a$ |
| A5 | 11.18 ± 0.59 | 13.88 ± 0.22$^a$ |
| A6 | 10.75 ± 0.65 | 14.02 ± 0.31$^a$ |

$^a p < 0.05$

TABLE 4

Levels of Hematocrit in Groups (A0) to (A6)

| Groups | Hematocrit (%) | |
|---|---|---|
| | Day 0 | Day 7 |
| A0 | 46.13 ± 3.78$^a$ | 45.82 ± 3.95$^a$ |
| A1 | 22.65 ± 2.18 | 21.83 ± 2.13 |
| A2 | 23.63 ± 2.93 | 35.18 ± 2.27$^a$ |
| A3 | 22.42 ± 2.15 | 34.48 ± 4.22$^a$ |
| A4 | 20.92 ± 2.36 | 36.50 ± 4.02$^a$ |
| A5 | 20.78 ± 3.09 | 39.52 ± 3.11$^a$ |
| A6 | 20.56 ± 3.11 | 40.30 ± 3.35$^a$ |

$^a p < 0.05$

It is suggested that the herbal extract of the present invention has potential to be applied to the pharmaceutical industry, being an active substance of medication or health products for anemia. In the present invention, the herbal extract can be given to any target individually or combined with any acceptable excipients, for example carriers or other ingredients, and is capable of being further manufactured into any form of medicament, such as pill, capsule, powder, solution and pastil for easy and convenient delivery to targets. Preferably, the medication of the present invention comprises mulberry and *Acanthopanax senticosus* in a weight ratio of 2:1 to 1:2, particularly to 2:1, and is preferably delivered to the target once a day, with a dosage of 1.0 g per kilogram of body weight and with a period of treatment lasting for 1 week.

In summary, through the present invention, a manufacture method of a herbal extract for anemia comprising mulberry and *Acanthopanax senticosus* in a weight ratio of 2:1 to 1:2 via an easy, convenient and time-and-cost saving process. With the herbal extract of the present invention, a medication or health product comprising the herbal extract is also easily obtained. The herbal extract has natural medical properties in anemia, and will be easy to put to use in the pharmaceutical industries. In this way, the herbal preparations will become easy to take and be more popular and acceptable to the general public.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A method of treating anemia comprising administering an effective amount of a herbal extract to a subject in need thereof, wherein the herbal extract is manufactured by a manufacture method comprising:

drying, by providing a herbal material comprising dry mulberry and dry *Acanthopanax senticosus*, with the water content of the herbal material being lower than 10%, wherein the dry *Acanthopanax senticosus* is obtained by soaking *Acanthopanax senticosus* in rice wine for 22 to 26 hours, decocting the *Acanthopanax senticosus* at high pressure and high temperature to obtain a decoction of *Acanthopanax senticosus*, and then drying the decoction of *Acanthopanax senticosus*;

extracting, by soaking the herbal material into a solvent to obtain a liquid extract, wherein the weight ratio between the herbal material and the solvent is 1:10 to 1:5; and condensation, by condensing the liquid extract to obtain the herbal extract.

2. The method of treating anemia as defined in claim 1, wherein the weight ratio between the dry mulberry and the dry *Acanthopanax senticosus* is 2:1 to 1:2.

3. The method of treating anemia as defined in claim 1, wherein the solvent is water, methanol, ethanol, acetone, ethane, propane, butane, hexane, petroleum, or benzene.

4. The method of treating anemia as defined in claim 1, wherein extracting is processed via sonication.

5. The method of treating anemia as defined in claim 1, wherein drying is processed via lyophilization, spray drying, evaporation or heating drying.

6. The method of treating anemia as defined in claim 1, wherein condensation is processed via evaporation, or heating drying.

7. The method of treating anemia as defined in claim 1, wherein the herbal extract is orally administered to the subject in need.

8. The method of treating anemia as defined in claim 1, wherein the herbal extract is orally administered in a dosage of 1.0 g/per kilogram of body weight of the subject in need.

* * * * *